United States Patent
Babaev

(10) Patent No.: US 8,562,547 B2
(45) Date of Patent: **\*Oct. 22, 2013**

(54) METHOD FOR DEBRIDING WOUNDS

(76) Inventor: Eliaz Babaev, Minnetonka, MN (US)

( * ) Notice: Subject to any disclaimer, the term of this patent is extended or adjusted under 35 U.S.C. 154(b) by 1312 days.

This patent is subject to a terminal disclaimer.

(21) Appl. No.: 12/060,486

(22) Filed: Apr. 1, 2008

(65) Prior Publication Data

US 2008/0183109 A1    Jul. 31, 2008

Related U.S. Application Data

(63) Continuation-in-part of application No. 11/857,162, filed on Sep. 18, 2007, now Pat. No. 7,785,278, and a continuation-in-part of application No. 11/449,220, filed on Jun. 7, 2006, now Pat. No. 7,431,704.

(51) Int. Cl.
*A61H 1/00* (2006.01)
*A61B 17/32* (2006.01)

(52) U.S. Cl.
USPC .............................................. 601/2; 606/169

(58) Field of Classification Search
USPC ........... 606/39, 167, 169, 190; 601/2; 604/22; 600/437
See application file for complete search history.

(56) References Cited

U.S. PATENT DOCUMENTS

| | | |
|---|---|---|
| 3,275,059 A | 9/1966 | McCullough |
| 3,392,916 A | 7/1968 | Engstrom et al. |
| 3,561,444 A | 2/1971 | Boucher |
| 3,860,173 A | 1/1975 | Sata |
| 4,052,004 A | 10/1977 | Martin et al. |
| 4,085,893 A | 4/1978 | Durley, III |
| 4,153,201 A | 5/1979 | Berger et al. |
| 4,251,031 A | 2/1981 | Martin et al. |
| 4,271,705 A | 6/1981 | Crostack |
| 4,294,407 A | 10/1981 | Reichl et al. |
| 4,301,093 A | 11/1981 | Eck |
| 4,301,968 A | 11/1981 | Berger et al. |
| 4,309,989 A | 1/1982 | Fahim |
| 4,319,155 A | 3/1982 | Nakai et al. |
| 4,334,531 A | 6/1982 | Reichl et al. |
| 4,352,459 A | 10/1982 | Berger et al. |
| 4,428,531 A | 1/1984 | Martin |
| 4,466,571 A | 8/1984 | Muhlbauer |
| 4,530,360 A | 7/1985 | Duarte |
| 4,541,564 A | 9/1985 | Berger et al. |

(Continued)

OTHER PUBLICATIONS

Isakov, U; Loshcilov, V; Kleimenov, V; Babaev, E., First Experience of Using New Ultrasound Instrument for Treating Biological Tissue. Ultrasound in Surgery, Proceedings of Moscow Bauman School. 1st Ed. No. 165. 1973. p. 57-59.

(Continued)

*Primary Examiner* — Tuan V Nguyen
(74) *Attorney, Agent, or Firm* — Winthrop & Weinstine, P.A.

(57) ABSTRACT

A method enabling relatively pain-free wound debridement is provided. The method entails double-delivering ultrasound to the wound and dissecting material to be debrided with a cutting edge. Delivering ultrasound energy via a coupling medium to an area of the wound within the vicinity of the material to be debrided and exposing the material to be debrided to ultrasound vibrations as to induce vibrations about the point of dissection, the double-delivery of ultrasound elicits an effect allowing for relatively pain-free debridement. While the effect elicited by the double-delivery is in place, the material to be debrided is dissected with a cutting edge.

20 Claims, 2 Drawing Sheets

(56) References Cited

U.S. PATENT DOCUMENTS

| | | | |
|---|---|---|---|
| 4,582,654 A | 4/1986 | Karnicky et al. | |
| 4,619,400 A | 10/1986 | Van Der Burgt | |
| 4,642,581 A | 2/1987 | Erickson | |
| 4,655,393 A | 4/1987 | Berger | |
| 4,659,014 A | 4/1987 | Soth et al. | |
| 4,679,551 A | 7/1987 | Anthony | |
| 4,726,523 A | 2/1988 | Kokubo et al. | |
| 4,726,525 A | 2/1988 | Yonekawa et al. | |
| 4,733,820 A | 3/1988 | Endo et al. | |
| 4,756,478 A | 7/1988 | Endo et al. | |
| 4,783,003 A | 11/1988 | Hirabayashi et al. | |
| 4,790,479 A | 12/1988 | Matsumoto et al. | |
| 4,793,339 A | 12/1988 | Matsumoto et al. | |
| 4,832,683 A * | 5/1989 | Idemoto et al. | 604/22 |
| 4,850,534 A | 7/1989 | Takahashi et al. | |
| 4,877,989 A | 10/1989 | Drews et al. | |
| 4,905,671 A | 3/1990 | Senge et al. | |
| 4,930,700 A | 6/1990 | McKown | |
| 4,941,618 A | 7/1990 | Hildebrand et al. | |
| 4,961,885 A | 10/1990 | Avrahami et al. | |
| 5,002,059 A | 3/1991 | Crowley et al. | |
| 5,040,537 A | 8/1991 | Katakura | |
| 5,063,922 A | 11/1991 | Hakkinen | |
| 5,076,266 A | 12/1991 | Babaev | |
| 5,104,042 A | 4/1992 | McKown | |
| 5,115,805 A | 5/1992 | Bommannan et al. | |
| 5,134,993 A | 8/1992 | van der Linden et al. | |
| 5,163,433 A | 11/1992 | Kagawa et al. | |
| 5,172,692 A | 12/1992 | Kulow et al. | |
| 5,186,162 A | 2/1993 | Talish et al. | |
| 5,197,946 A | 3/1993 | Tachibana | |
| 5,211,160 A | 5/1993 | Talish et al. | |
| 5,231,975 A | 8/1993 | Bommannan et al. | |
| 5,254,082 A | 10/1993 | Takase | |
| 5,269,291 A | 12/1993 | Carter | |
| 5,315,998 A | 5/1994 | Tachibana et al. | |
| 5,316,000 A | 5/1994 | Chapelon et al. | |
| 5,318,014 A | 6/1994 | Carter | |
| 5,323,769 A | 6/1994 | Bommannan et al. | |
| 5,324,255 A | 6/1994 | Passafaro et al. | |
| 5,345,940 A | 9/1994 | Seward et al. | |
| 5,347,998 A | 9/1994 | Hodson et al. | |
| 5,362,309 A | 11/1994 | Carter | |
| 5,374,266 A | 12/1994 | Kataoka et al. | |
| 5,380,411 A | 1/1995 | Schlief | |
| 5,393,296 A | 2/1995 | Rattner | |
| 5,431,663 A | 7/1995 | Carter | |
| 5,437,606 A | 8/1995 | Tsukamoto | |
| 5,474,071 A | 12/1995 | Chapelon et al. | |
| 5,515,841 A | 5/1996 | Robertson et al. | |
| 5,515,842 A | 5/1996 | Ramseyer et al. | |
| 5,516,043 A | 5/1996 | Manna et al. | |
| 5,520,166 A | 5/1996 | Ritson et al. | |
| 5,520,612 A | 5/1996 | Winder et al. | |
| 5,526,815 A | 6/1996 | Granz et al. | |
| 5,527,350 A | 6/1996 | Grove et al. | |
| 5,529,572 A | 6/1996 | Spector | |
| 5,545,124 A | 8/1996 | Krause et al. | |
| 5,551,416 A | 9/1996 | Stimpson et al. | |
| 5,554,172 A | 9/1996 | Horner et al. | |
| 5,556,372 A | 9/1996 | Talish et al. | |
| 5,573,497 A | 11/1996 | Chapelon | |
| 5,616,140 A | 4/1997 | Prescott | |
| 5,626,554 A | 5/1997 | Ryaby et al. | |
| 5,643,179 A | 7/1997 | Fujimoto | |
| 5,656,016 A | 8/1997 | Ogden | |
| 5,658,323 A | 8/1997 | Miller | |
| 5,699,805 A | 12/1997 | Seward et al. | |
| 5,707,402 A | 1/1998 | Heim | |
| 5,707,403 A | 1/1998 | Grove et al. | |
| 5,720,287 A | 2/1998 | Chapelon et al. | |
| 5,730,705 A | 3/1998 | Talish et al. | |
| 5,735,811 A | 4/1998 | Brisken | |
| 5,743,863 A | 4/1998 | Chapelon | |
| 5,752,924 A | 5/1998 | Kaufman et al. | |
| 5,762,616 A | 6/1998 | Talish | |
| 5,785,972 A | 7/1998 | Tyler | |
| 5,835,678 A | 11/1998 | Li et al. | |
| 5,843,139 A | 12/1998 | Goedeke et al. | |
| 5,879,314 A | 3/1999 | Peterson et al. | |
| 5,879,364 A | 3/1999 | Bromfield et al. | |
| 5,882,302 A | 3/1999 | Driscoll, Jr. et al. | |
| 5,894,841 A | 4/1999 | Voges | |
| 5,895,362 A | 4/1999 | Elstrom et al. | |
| 5,947,921 A | 9/1999 | Johnson et al. | |
| 5,960,792 A | 10/1999 | Lloyd et al. | |
| 5,989,245 A | 11/1999 | Prescott | |
| 6,001,069 A | 12/1999 | Tachibana et al. | |
| 6,007,499 A | 12/1999 | Martin et al. | |
| 6,014,970 A | 1/2000 | Ivri et al. | |
| 6,024,718 A | 2/2000 | Chen et al. | |
| 6,026,808 A | 2/2000 | Armer et al. | |
| 6,027,495 A | 2/2000 | Miller | |
| 6,041,253 A | 3/2000 | Kost et al. | |
| 6,061,597 A | 5/2000 | Rieman et al. | |
| 6,076,519 A | 6/2000 | Johnson | |
| 6,083,159 A | 7/2000 | Driscoll, Jr. et al. | |
| 6,095,141 A | 8/2000 | Armer et al. | |
| 6,098,620 A | 8/2000 | Lloyd et al. | |
| 6,102,298 A | 8/2000 | Bush et al. | |
| 6,104,952 A | 8/2000 | Tu et al. | |
| 6,106,547 A | 8/2000 | Huei-Jung | |
| 6,113,558 A | 9/2000 | Rosenschein et al. | |
| 6,113,570 A | 9/2000 | Siegel et al. | |
| RE36,939 E | 10/2000 | Tachibana et al. | |
| 6,158,431 A | 12/2000 | Poole | |
| 6,176,839 B1 | 1/2001 | DeLuis et al. | |
| 6,186,963 B1 | 2/2001 | Schwarze et al. | |
| 6,190,315 B1 | 2/2001 | Kost et al. | |
| 6,190,336 B1 | 2/2001 | Duarte et al. | |
| 6,206,842 B1 | 3/2001 | Tu et al. | |
| 6,206,843 B1 | 3/2001 | Iger et al. | |
| 6,231,528 B1 | 5/2001 | Kaufman et al. | |
| 6,234,990 B1 | 5/2001 | Rowe et al. | |
| 6,251,099 B1 | 6/2001 | Kollias et al. | |
| 6,273,864 B1 | 8/2001 | Duarte et al. | |
| 6,296,630 B1 | 10/2001 | Altman et al. | |
| 6,314,318 B1 | 11/2001 | Petty | |
| 6,321,109 B2 | 11/2001 | Ben-Haim et al. | |
| 6,322,527 B1 | 11/2001 | Talish | |
| 6,325,769 B1 | 12/2001 | Klopotek | |
| 6,371,903 B1 | 4/2002 | Blanc et al. | |
| 6,478,754 B1 | 11/2002 | Babaev | |
| 6,533,803 B2 | 3/2003 | Babaev | |
| 6,569,099 B1 | 5/2003 | Babaev | |
| 6,601,581 B1 | 8/2003 | Babaev | |
| 6,623,444 B2 | 9/2003 | Babaev | |
| 6,663,554 B2 | 12/2003 | Babaev | |
| 6,716,184 B2 | 4/2004 | Vaezy et al. | |
| 6,723,064 B2 | 4/2004 | Babaev | |
| 6,761,729 B2 | 7/2004 | Babaev | |
| 6,799,729 B1 * | 10/2004 | Voic | 239/102.2 |
| 6,916,296 B2 | 7/2005 | Soring et al. | |
| 7,025,735 B2 | 4/2006 | Soring et al. | |
| 2004/0030254 A1 * | 2/2004 | Babaev | 600/459 |
| 2006/0241470 A1 | 10/2006 | Novak et al. | |
| 2006/0241533 A1 | 10/2006 | Geller | |

OTHER PUBLICATIONS

Hsieh, Yueh-Ling, Effects of Ultrasound and Diclofenac Phonophoresis on Inflammatory Pain Relief: Suppression of Inducible Nitric Oxide Synthase in Arthritic Rats. Physical Therapy, vol. 86(1): 39-49. Jan. 2006.

Babaev et al., First Experience of Using New Ultrasound Instrument for Treating Biological Tissue, article, 1973, pp. 57-59, 1st Ed. No. 165, Moscow Bauman School, Moscow, Russia.

Babaev, The Qoustic Wound Therapy System (displaying model wound), sales literature released to the public Apr. 19, 2007.

* cited by examiner

METHOD FOR DEBRIDING WOUNDS

CROSS REFERENCE TO ELATED APPLICATIONS

This application is a continuation-in-part of U.S. patent application Ser. No. 11/857,162 filed Sep. 18, 2007, now U.S. Pat. No. 7,785,278, the teachings of which are hereby incorporated by reference.

This application is also a continuation-in-part of U.S. patent application Ser. No. 11/449,220 filed Jun. 7, 2006, now U.S. Pat. No. 7,431,704, the teaching of which are hereby incorporated by reference.

BACKGROUND OF THE INVENTION

1. Field of the Invention

The present invention relates to a method for debriding wounds and/or dissecting tissues from the body.

2. Description of the Related Art

When confronted with wounded tissue, physicians and similar practitioners of the medical arts may rely on numerous methods to treat the wound. Despite the repertoire of available techniques, treating severe and/or chronic wounds can be especially difficult. To assist in healing, the practitioner may have to resort to surgical debridement. During debridement, the practitioner removes material from a wound to expose healthy and/or granulation tissue. It is generally believed that keeping such tissue exposed expedites wound healing. However, as wounds begin to heal after debridement, additional material may collect over the healthy and/or granulation tissue. Successful treatment, therefore, often requires repeated debridement.

A diverse amount of material may be removed from the wound during debridement. The removed material may include improper healed, dead, and/or dying tissue. However, the material removed is not limited to tissue. For instance, foreign substances such as, but not limited to, dirt, debris, and/or infectious agents may collect within the wound. In the case of an infectious agent such as, but not limited to, a bacteria, a bacterial laden biofilm may develop over the wound covering healthy and/or granulation tissue. As the infection increases in severity, the wound may become covered with gangrenous tissue. Exposing healthy and/or granulation tissue would then require the removal of such containments. Accordingly, foreign contaminants, biofilms, and/or gangrenous tissue may represent material that has to be debrided from the wound.

In combination or in the alternative, the trauma and/or pathological conditions creating the wound may generate material that needs to be removed to expose healthy and/or granulation tissue. The trauma responsible for creating the wound may fracture blood vessels supplying tissue surviving the trauma. Fracturing the blood vessels, the trauma reduces the blood supply to the surviving tissue creating a region of ischemic tissue. Ischemia may also be the result of various conditions such as, but not limited, diabetes and/or various vascular diseases. As the ischemia persists, the tissue becomes deprived of vital nutrients required for growth and/or survival, and thus may eventually becomes devitalized. Failing to receive required nutrients, the devitalized tissue may eventually slip into a non-viable state. The non-viable tissue may begin a process of necrosis and/or apoptosis in which the cells of the non-viable tissue release various factors the digest and/or degrade the tissue. Destroying itself, the non-viable tissue becomes necrotic tissue. If the degradation and/or digestive process continues beyond the point of cellular death, the necrotic tissue may become slough. However, it is also possible that digestion and/or degradation stops with cellular death as to create an eschar over the wound. Regardless of how far the tissue progresses from ischemia and/or devitalization to slough and/or eschar, the dead and dying tissue generated from a trauma and/or pathological condition responsible for the wound should be removed.

In combination or in the alternative, the wounds may also generate material that needs to be removed to expose healthy and/or granulation tissue. For instance, in response to an inflammation brought about by the presence of foreign substances and/or trauma an exudate may be secreted. As the secretion of exudate persists, the wound may become covered by various proteins and/or other molecules manufactured by the body. Secretion of a fibrinous exudate, for example, may lead to a build up fibrin over the wound. Regardless of the type of exudate secreted and/or built up over the wound, this body generated material should be removed during debridement.

In combination or in the alternative, improperly healed tissue may have to be removed from the wound. For example, instead of migrating into the wound, cells responsible for closing the wound and/or replacing lost tissue may begin to migrate away from the wound. Such misdirected migration may hinder and/or prevent proper closure and/or healing of the wound. Placing cellular migration on the proper path may require removing the tissue created as a result of the misdirected migration. Otherwise healthy tissue hindering, preventing, or otherwise retarding proper closure and/or healing of the wound may appear through other means. Regardless of its origin and/or condition, tissue retarding closure and/or healing should be removed during debridement.

Debriding a wound to expose healthy and/or granulation tissue and/or remove tissue retarding proper closure and/or healing is generally done to expedite wound healing. Exposing debrided wounds to ultrasound has also been shown to expedite wound healing. As to capitalize on this phenomenon, various debridement techniques with ultrasonically vibrating instruments have been developed. Typically these techniques entail removing various materials from the wound with ultrasonically vibrating dissection devices, while simultaneously exposing the wound to ultrasound. Accordingly the wound receives beneficial ultrasound while it is debrided.

SUMMARY OF THE INVENTION

Treating severe and/or chronic wounds can be especially difficult. Successful treatment often requires repeated debridement. The painful nature of surgical debridement, however, often results in poor patient compliance. Rather than enduring the pain of treatment, patients opt to leave the wound untreated. In the case of infected and/or inflamed wounds, surgical debridement may be even more painful, resulting in lower rates of patient compliance. An untreated wound becomes at risk for developing an infection and/or other complications. As the complications increase in severity, the patient may experience a reduced quality of life. For instance, an untreated diabetic foot ulcer on a patient's foot may become so painful that the patient has difficulty walking.

A method enabling relatively pain-free wound debridement is provided. The method comprises a double delivery of ultrasound to the wound and dissection of the material to be debrided with a cutting edge. The double-delivery of ultrasound elicits an effecting allowing for relatively pain free debridement by delivering ultrasound energy via a coupling medium to an area of the wound within the vicinity of the material to be debrided and exposing the wound to ultrasound vibrations as to induce vibrations about the point of dissection. While the effect elicited by the double-delivery is in place, the material to be debrided is removed, fragmented, and/or otherwise dissected with a cutting edge.

The double-delivery ultrasound exposes one point and/or region of the wound to ultrasound energy and the material about the point of dissection to ultrasound vibrations. Collectively, the double-delivery's dual exposure elicits an effect allowing for relatively pain-free debridement. Exposing the wound to one of the ultrasound deliveries without the other will not allow for relatively pain-free debridement. Consequently, it is the combined effects elicited by the delivery of ultrasound energy and ultrasound vibrations at differing points that allows for relatively pain-free wound debridement. One delivery does not necessarily have to precede the other. Consequently, the exposure to ultrasound may occur before, subsequently to, and/or simultaneously with the exposure to vibrations. Because it is the additive effect elicited by both deliveries that allows for relatively pain-free dissection with a cutting edge, the second delivery should occur before the effects elicited by the first delivery have dissipated. Likewise, dissection of the material to be debrided should occur while the effects elicited from the double-delivery are in place.

One of the deliveries exposes an area of the wound in the vicinity of the tissue to be debrided to ultrasound energy. Accordingly, an area of the wound close to, neighboring, and/or surrounding the material to be debrided is exposed to ultrasound energy. When exposing the wound to ultrasound energy it is important that a sufficient amount of energy is transferred to the wound without excessively injuring the wound. Injuring the wound may induce physiological responses, such as, but not limited to, the release of various inflammatory factors and/or mediators, counteracting the effects elicited by the double-delivery of ultrasound. Delivering a sufficient amount of ultrasound energy without excessively injuring the wound can be accomplished by delivering the energy via a coupling medium. Any fluid and/or atomized spray capable of conducting ultrasound energy that is not unduly toxic to the tissue may be utilized as a coupling medium. For instance fluids such as, but not limited to, saline, water, alcohol, corn oil, and/or vegetable oil may be utilized. The coupling medium acts as a conduit for the transmission and delivery of ultrasound energy to the wound.

The other delivery of the double-delivery exposes material about the point of dissection to ultrasound vibrations. Exposing the material to ultrasound vibrations induces vibrations within the material. Confining the vibrations induced may enhance the effects produced by this delivery. One possible manner of inducing vibrations within a confined region about the point of dissection is to expose the material about the point of dissection to ultrasound vibrations released from an ultrasound horn having a consistent and narrow diameter. In combination or in the alternative. vibrations may be induced within a confined region about the point of dissection by exposing the material about the point of dissection to concentrated ultrasound vibrations. Concentrating ultrasound vibrations can be accomplished by inducing an ultrasound horn with a larger cross section at its proximal end than its distal end to vibrate. As the vibrations travel from the horn's wide proximal end to the narrow distal end, the amplitude of the vibrations increase while their frequency remains constant. Placing the narrow distal end in contact with the material about the point of dissection exposes this confined region of the tissue to ultrasound vibrations. Due to this direct contact exposure, vibrations are induced in the confined region about the point of dissection. Accordingly, exposing the wound to concentrated ultrasound vibrations induces vibrations within a confined region encompassing the point of dissection.

The horn utilized to concentrate the ultrasound vibrations may be constructed from any material capable of conducting ultrasound vibrations such as, but not limited to, aluminum, stainless steel, titanium, and any combination thereof. Preferably, the horn is constructed from titanium alloy Ti 6A1-4V. It is also preferable that the distal end of the horn used to concentrate the vibrations contains a sharpened structure such as, but not limited to, an edge and/or point. Though sharpened to some degree, the sharpened structure need not be so sharp as to be capable of easily cutting and/or debriding tissue.

While the effect elicited by the double-delivery is in place, the material to be debrided is dissected with a cutting edge. Any structure containing an edge and/or point sufficiently fine as to enable dissection may be used as the cutting device. Accordingly, a horn utilized to expose the material about the point of dissection to ultrasound vibrations may be used as the cutting device if it contains a sufficiently fine edge and/or point. An advantage of using the horn as the cutting devices is that it simplifies procedure. Possessing a structure sufficiently sharp to enable dissection, the horn may be used to expose the material about the point of dissection to ultrasound vibrations and then used to dissect the material to be debrided. Consequently, the practitioner debriding the wound need not change instruments as he transitions between operations of the procedure. The procedure could be further simplified by utilizing the same structure of a horn to expose the material about the point of dissection to ultrasound vibrations and simultaneously dissect the material to be debrided. According, the practitioner would be able to perform two operations of the procedure with a single movement. It should be noted that the vibrations induced in the cutting edge of a horn may increase the cutting edges ability to dissect tissue, allowing a blunter edge to be utilized.

The effects elicited by the double-delivery of ultrasound reduce the patient's physiological perception pain while the wound is debrided. However, the perception of pain also involves a psychological component. For instance, when a patient believes something will hurt, he may perceive the slightest sensation as painful. Consequently, if the patient believes debridement will be painful he will perceive pain though the double-delivery has diminished the physiological perception of pain. Of course, comforting words by the medical practitioner may reduce the patient's expectation of pain. Despite being comforted by the practitioner, the medical environment in which the invention is practiced may still make the patient anxious. Unable to overcome his anxiety, the patient may still perceive pain. However, due to the physiological effects elicited by the double-delivery the pain perceived will be primarily psychological. Accordingly, the present inventions allows for relatively pain-free wound debridement.

BRIEF DESCRIPTION OF THE DRAWINGS

The present invention will be shown and described with reference to the drawings of preferred embodiments and clearly understood in its details. Like elements of the various embodiments depicted within the figures are equivalently numbered.

DETAILED DESCRIPTION OF THE INVENTION

The method of the present invention will be described with reference to the surgical apparatus depicted in FIGS. 1 and 2. It should be appreciated that devices other than the surgical apparatus depicted in FIGS. 1 and 2 may be used to practice the invention. For instance, pending U.S. patent applications Ser. Nos. 11/449,220 and 11/857,162 depict devices that may be used to practice the invention, the teachings of which have been previously incorporated by reference.

Figure 1:
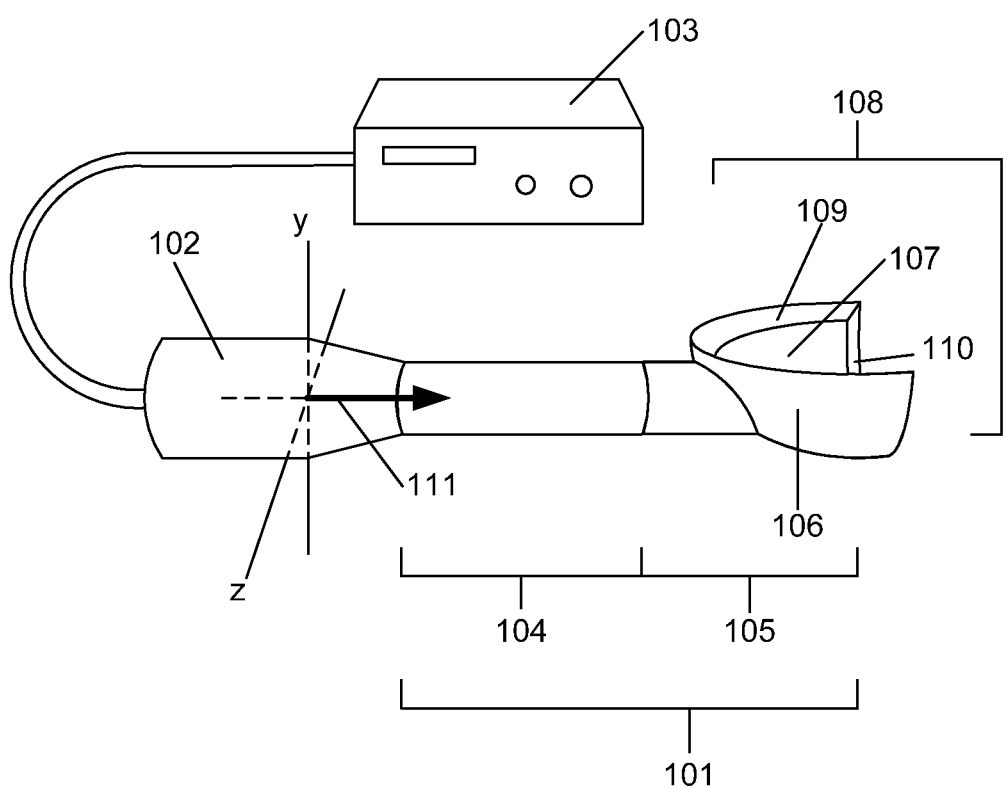
FIG. 1 displays a three-dimensional view of a surgical apparatus that may be used to practice the present invention.

FIG. 1 displays a three-dimensional view of a surgical apparatus that may be used to practice the present invention. The advantage of using the surgical apparatus depicted in FIG. 1 is that the double-delivery of ultrasound and dissection may be performed with a single motion. The surgical apparatus comprises a surgical substructure 101 attached to an ultrasound transducer 102 driven by an electrical signal produced by generator 103. Surgical substructure 101 is comprised of shaft 104 and tip 105. Tip 105, in turn, comprises radial surface 106 and a cavity 107 containing an opening 108. Encircling opening 108 are two cutting edges 109 and 110. Radial cutting edge 109 encircles the upper portion of opening 108, while distal cutting edge 110 encircles the distal portion opening of 108.

Mechanically coupled to transducer 102 and tip 105, shaft 104 transmits ultrasonic vibrations generated by transducer 102 to tip 105. Accordingly, when driven or otherwise activated by generator 103, transducer 102 induces ultrasonic vibrations within the surgical substructure 101. Inducing vibrations in substructure 101 causes ultrasound to be released from walls of cavity 107 and cutting edges 109 and 110. Transmitting vibrations and releasing ultrasound, surgical substructure 101 may be classified as an ultrasound horn.

Generator 103 should be capable of producing an electrical signal of a sufficient voltage to drive transducer 102 to induce substructure 101 to vibrate, preferably in resonance with the amplitude of the vibrations being between approximately 1 micron and approximately 250 microns. Surgical substructure 101 may be capable of vibrating approximately in resonance at a frequency between approximately 15 kHz and approximately 5 MHz. Preferably, substructure 101 should be capable of vibrating approximately in resonance at a frequency of approximately 30 kHz.

Figure 2:
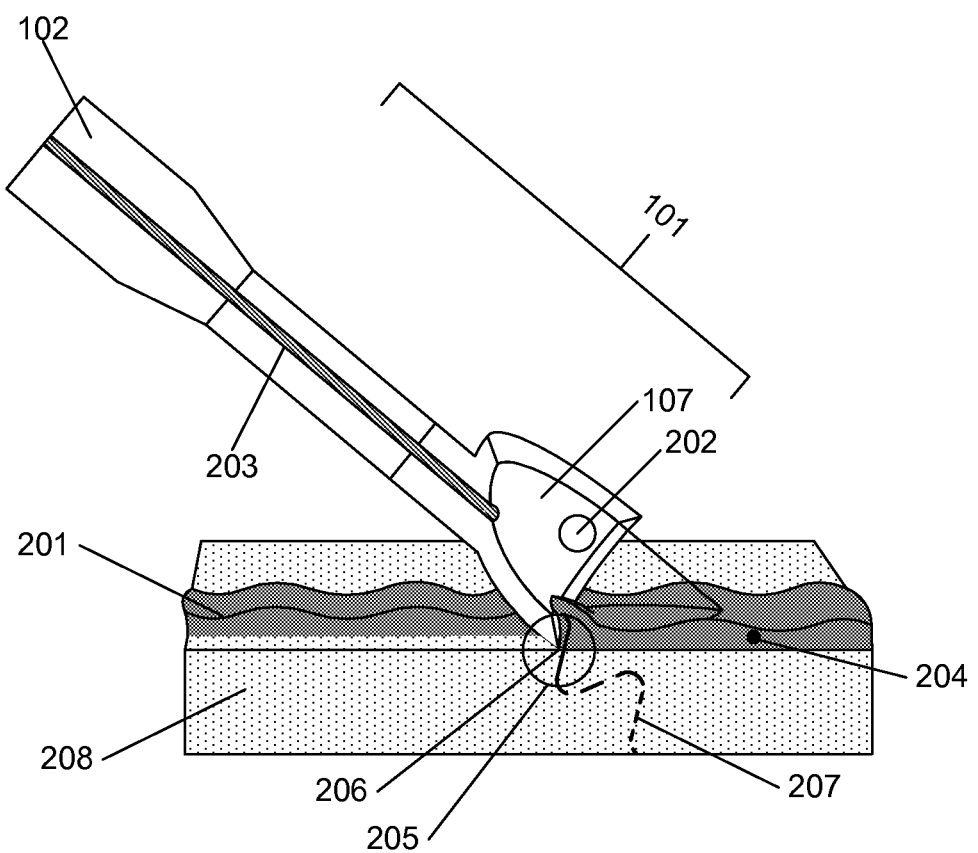
FIG. 2 depicts practice of the present invention with the surgical apparatus depicted in FIG. 1.

FIG. 2 depicts practice of the present invention with the surgical apparatus depicted in FIG. 1. To facilitate the delivery of ultrasound energy to an area of the wound within the vicinity of the material to be debrided, a coupling medium 202 is delivered to cavity 107 through channel 203, which extends through transducer 102 and shaft 104 before opening into cavity 107. After entering cavity 107 coupling medium 202 is atomized and/or broken into droplets and sprayed towards the tissue by the ultrasound emanating from the walls of cavity 107. The spray produced from coupling medium 202 serves as a conduit for the transmission of ultrasound energy emanating from walls of cavity 107, thereby delivering ultrasound energy to the wound. Delivering a sufficient amount of ultrasound energy to the wound without inducing excessive injury can also be accomplished by delivering the energy via a coupling medium that is not atomized and/or broken into droplets. Accordingly, atomizing and/or breaking the coupling medium into droplets is not necessary.

Regardless of whether the coupling medium 202 is atomized or not, the delivery of ultrasound energy to an area of the wound within the vicinity of the material to be debrided elicits a portion of the effects needed for relatively pain-free wound debridement. Additionally, the delivered ultrasound energy may enhance debridement by inducing cavitations within the coupling medium 202 pooling and/or otherwise collecting in and/or over the wound to be treated. Inducing cavitations in the coupling medium results in the formation of tiny bubbles. Conceptually, this phenomenon is similar to inducing water to boil by applying heat. However, the induction of cavitations within the coupling medium by the ultrasound energy delivered to the tissue is not dependant upon heating the coupling medium to its boiling point. As such, the induction of cavitations is not dependent upon the transfer of thermal energy to the coupling medium.

After spontaneously forming within the coupling medium, the cavitations randomly explode and/or collapse. An exploding and/or collapsing cavitation releases energy into the coupling medium surrounding it. Furthermore, the explosion and/or collapse of a cavitation induces a pressure change within the volume of the coupling medium surrounding the cavitation. The pressure change and/or energy released may loosen the tissue to be debrided. In the alternative or in combination, infectious agent within the vicinity of the exploding and/or collapsing cavitation may be inactivated, killed, weakened, and/or otherwise compromised.

If transducer 102 is a piezoelectric transducer and induces surgical substructure 101 to vibrate approximately in resonance, then the voltage of the electrical signal supplied by generator 103 will largely control the degree to which the coupling medium 202 is cavitated and/or atomized. At low voltages coupling medium 202 will be cavitated to a small degree. As the voltage increases, the amount of cavitations within coupling medium 202 increases. Likewise, as the voltage increases the degree to which coupling medium 202 is atomized will also increase. Regardless, of whether coupling medium 202 is atomized and/or cavitated, the presence of coupling medium 202 enables a sufficient amount of ultrasound energy to be delivered to an area of the wound within the vicinity of the material to be debrided without excessively injuring the wound.

The delivery of ultrasound energy to an area of the wound within the vicinity of the material to be debrided elicits a portion of the effects allowing for relatively pain-free wound debridement. This delivery of ultrasound is suspected, but not known, to change the permeability of cellular membranes to ions and/or other molecules within the extracellular environment. Changing membrane permeability may disrupt ionic and/or other chemical gradients relied upon by the cells to respond to painful stimuli. Concentrating the ultrasound energy delivered about a point within the wound in the vicinity of the material to be debrided may elicit a greater change in membrane permeability of cellular structures such as, but not limited to, dendrites, axon, and/or somas, possibly enhancing one of the elicited effects of the double-delivery.

Concentrating the energy delivered to the wound may be accomplished with any radiation surface from which ultrasonic waves of converging trajectories are emitted. Ultrasonic waves emanating from the radiation surface of ultrasound horn carry ultrasound energy. When one wave crosses the path of another wave the energy carried by the waves becomes concentrated about the point of intersection. Accordingly, an ultrasound emitting surface of an ultrasound horn may be formed in variety of configurations that allow for the delivery of concentrated ultrasound energy to an area of the wound within the vicinity of the material to be debrided. Cavity 107 of the surgical apparatus depicted in FIGS. 1 and 2 illustrates one of the many possible configurations.

Forming a parabola about two axes, the walls of cavity 107 form a paraboloid structured radiation surface. The paraboloid structure directs the ultrasound energy emanating the walls of cavity 107 towards the focal point 204 of the parabola, thereby concentrating the energy about the focal point 204. The surgical apparatus, as depicted in FIG. 2, may be oriented such that focal point 204 is positioned on or below the surface of wound as to concentrate the ultrasound energy delivered about a point within the wound in the vicinity of the material to be debrided.

Delivering concentrated ultrasound energy to the wound does not necessarily require utilizing a paraboloid structured radiation surface. Radiation surfaces of various configurations, readily recognizable by those skilled in the art, may be utilized in combination with or in the alternative to a paraboloid configuration.

Delivering ultrasound energy to an area of the wound within the vicinity of the material to be debrided only elicits a portion of effects allowing for relatively pain-free wound debridement. In and of itself, the delivery of ultrasound energy to an area of the wound within the vicinity of the material to be debrided is insufficient to allow for relatively pain-free wound debridement. Accordingly, it is also necessary to induce vibrations within a confined region of the material 205 about the point of dissection 206. Directly contacting the material about the point of dissection 206 with vibrating cutting edges 109 and/or 110 induces vibrations within the confined region 205, thereby accomplishing the other delivery of the double-delivery.

When driven or otherwise activated by generator 103, transducer 102 induces ultrasonic vibrations within the surgical substructure 101. Mechanically coupled to transducer 102 and tip 105, shaft 104 transmits ultrasonic vibrations generated by transducer 102 to tip 105. Accordingly, ultrasound vibrations generated by transducer 102 are channeled into cutting edges 109 and 110. Placing the narrow sharpened edges of cutting edges 109 and/or 110 in close proximity to the point of dissection 206 exposes material within the confined region 205 to ultrasound vibrations. Due to this direct contact exposure, vibrations represented by sine wave 207, are induced within the material about the point of dissection 206. As the vibrations 207 travel away from the point of exposure their amplitude decreases. Eventually a distance is reached in which the material is no longer vibrated. Consequently, the direct exposure to the vibrations released from cutting edges 109 and/or 110 induces vibrations within confined region of the tissue 205 about the point of dissection 206.

The delivery of ultrasound vibrations to the confined region 205 elicits a portion of the effects allowing for relatively pain-free debridement. Inducing vibrations within the confined region 205 about the point of dissection 206 is suspected, but not known to weaken adhesion such as, but not limited to cellular adhesion, holding the material to be debrided together and/or to wound. Weakening the adhesion holding the material to the wound may allow the material to be debrided to be dissected with reduced levels of tissue and/or cellular damage. In combination or the alternative, inducing vibrations within the material to be debrided may weaken the adhesion holding the material together causing the material to fragment and/or otherwise separate from itself. Consequently, the induced vibrations 207 may allow the material to be debrided to be lifted away, pushed aside, fragmented, and/or otherwise dissected by cutting edges 109 and/or 110.

The sharpened edges of cutting edges 109 and/or 110 of an ultrasound horn induce vibrations 207 within confined region 205 about the point of dissection 206 by exposing the material about the point of dissection 206 to concentrated ultrasound vibrations. As the vibrations induced in the surgical substructure 101 by transducer 102 travel into the sharpened edges of cutting edges 109 and 110, they become concentrated. Accordingly, as the vibrations move towards the sharpened edges, their amplitude increases while their frequency remains constant. The surgical apparatus depicted in FIG. 2, therefore, induces vibrations 207 in the confined region 205 about the point of dissection 206 by exposing the material about the point of dissection 206 to concentrated ultrasound vibrations. It should be appreciated that exposing the wound to concentrated ultrasound vibrations is not necessary to effectuate the delivery of ultrasound resulting in the induction of vibrations in a confined region about the point of dissection. Rather, exposing the material about the point of dissection 206 to concentrated ultrasound vibrations is a consequence of dissecting the material to be removed with sharpened edges 109 and 110 while transducer 102 is activated.

Radial cutting edge 109 and/or distal cutting edge 110 may be used to dissect the material to be debrided. Because cavity 107 has a general paraboliod configuration, use of either cutting edge will allow for the delivery of ultrasound vibrations concentrated about a point within the wound in the vicinity of the tissue to be debrided. However, orientated differently with respect to the propagation path 111 of the ultrasound vibrations traveling through surgical substructure 101, cutting edges 109 and 110 expose the material about the point of dissection to different types of ultrasound vibrations. When transducer 102 is activated, vibrations are induced in surgical substructure 101. The induced vibrations travel away from transducer 102 towards the distal end of substructure 101 along propagation path 111. Orientated completely orthogonal to propagation 208, cutting edge 110 receives primarily longitudinal vibrations. According, when cutting edge 110 is used to dissect material a majority of the ultrasonic vibrations to which the material about the point of dissection is exposed will be comprised of longitudinal vibrations. Because the longitudinal vibrations received by cutting edge 110 will become concentrated as they travel towards its sharpened edge, a majority of the ultrasound vibrations to which the material is exposed to will be concentrated longitudinal vibrations.

Unlike cutting edge 110, cutting edge 109 is not orientated as to receive a significant amount of longitudinal vibrations. Orientated parallel to propagation path 111, vibrations traveling away from transducer 102 and towards the distal end of substructure 101 will not flow into cutting edge 109. However, this does not mean that cutting edge 109 is not receiving vibrations that become concentrated as they travel towards it sharpened edge. The vibrations induced in substructure 101 by the activation of transducer 102 cause substructure 101 to expand distally and rebound proximally. Consequently, the activation of transducer 102 causes substructure 101 to expand and contract about propagation path 111. As substructure 101 expands forward its width about the y and z axes decreases. Conversely, as substructure 101 rebounds backwards its width about the y and z axes increases. With its width decreasing and increasing, surgical substructure 101 experiences radial deflections about propagation path 111. Accordingly, the activation of transducer 102 induces longitudinal vibrations along propagation path 111 and radial vibrations about path 111 within surgical substructure 101.

Orientated parallel to propagation path 111, cutting edge 109 is positioned to receive radial vibrations. Propagating towards the periphery of surgical substructure 101 along paths orthogonal to propagation path 111, radial vibrations enter the base of cutting edge 109. According, when cutting edge 109 is used to dissect material a majority of the ultrasonic vibrations to which the material about the point of dissection is exposed will be comprised of radial vibrations. Because the radial vibrations received by cutting edge 109 will become concentrated as they travel towards its sharpened edge, a majority of the ultrasound vibrations to which the material is exposed to will be concentrated radial vibrations.

It should be appreciated that a cutting edge which is not orientated orthogonal to the propagation path of either the longitudinal or radial vibrations will receive both types of vibrations. Accordingly, such a cutting edge will expose the tissue about the point of dissection to both longitudinal and radial ultrasound vibrations. The proportion of radial and longitudinal waves to which the tissue about the point of dissection is exposed will depend on the orientation of the cutting edge. For instance, if the cutting edge is orientated at an angle of 45° to a propagation path of radial vibrations and longitudinal vibrations the edge will receive an equal portion of radial and longitudinal vibrations. As the vibrations received by the cutting edge travel towards its sharpened edge, they will become concentrated. Accordingly, the tissue about the point of dissection will be exposed to an equal portion of concentrated radial and longitudinal vibrations. Changing the orientation of the cutting edge will change the proportion of radial and longitudinal waves to which the tissue is exposed. As the orientation of the cutting edge becomes more orthogonal to the propagation path of one type of vibrations it will receive a larger portion of that type of vibration. Accordingly, a cutting edge orientated at an angle of 60° to a propagation path of radial vibrations and 30° to a propagation of longitudinal vibrations will receive a larger portion of radial than longitudinal vibrations. Consequently, the tissue about the point of dissection will be exposed to a larger portion of concentrated radial than longitudinal vibrations.

Inducing vibrations 207 within the confined region 205 about the point of dissection 206, cutting edges 109 and/or 110 are suspected to weaken adhesion holding the material to be debrided together and/or the wound. Weakening the adhesion may allow diseased and/or necrotic tissue 201 to be separated from healthy and/or viable tissue 208 below the point of dissection 206 with reduced levels of tissue and/or cellular damage. It should be appreciated that material other than diseased and/or necrotic tissue may be dissected. It should also be appreciated that material other than healthy and/or viable tissue may be spared.

Regardless of the material to be debrided and/or spared, moistening the wound with coupling medium 202 and/or any other fluid not unduly toxic to the tissue may facilitate inducing vibrations 207. Vibrations 207 are induced in the material about the point of dissection 206 by transferring the vibrations from cutting edges 109 and/or 110 to the material about the point of dissection 206. However, it is possible that the material about the point of dissection 206 may dampen the vibrations of cutting edges 109 and/or 110. Advancing edges 109 and/or 110 through the material within the wound may cause the material about the point of dissection 206 to come into direct contact with their edges. This will add mass to the cutting edges 109 and 110, thereby dampening their vibrations. Dampening the vibrations may lessen vibrations 207 transferred to the material about the point of dissection 206. It may, therefore, be beneficial to isolate at least the sharpened edges of cutting edges 109 and/or 110 from the material about the point of dissection 206.

Isolating cutting edges 109 and/or 110 from the material about the point of dissection 206 can be accomplished by moistening the wound. The wound may be moistened with coupling medium 202 and/or any other fluid capable of facilitating the transfer of vibrations from edges 109 and/or 110 to the material about the point of dissection 207, not unduly toxic to the tissue, such as, but not limited to, saline, water, vegetable oil, and/or alcohol. As cutting edges 109 and/or 110 advances through a moistened wound, the fluid utilized to moisten the wound flows between the cutting edges and the material about the point of dissection 206 preventing direct contact between the edges and the material. This allows cutting edges 109 and/or 110 to vibrate more freely. In addition to isolating cutting edges 109 and/or 110 from the material within the wound, the fluid moistening the wound may act as a conduit carrying vibrations from the cutting edges to and/or into the material about the point of dissection 206.

Exposing the material about the point of dissection 206 to concentrated ultrasound vibrations and dissecting the material to be debrided, cutting edges 109 and/or 110 induce vibrations in a confined region 205 about the point of dissection 206. Though it is necessary to induce vibrations in this region of the tissue by exposing the material about the point of the dissection to ultrasound vibrations in order to allow for relatively pain-free wound debridement, dissection need not be performed simultaneously with this ultrasound delivery. Rather, all that is required is that dissection be performed before the effects elicited by the delivery of ultrasound vibrations dissipate. Accordingly, the dissection may be performed after the ultrasound vibrations have been delivered to the material about the point of dissection.

If dissection and the delivery of ultrasound vibrations will not be performed by the same instruments, it may not be necessary to use the sharpened edge of an ultrasound horn to induce vibrations in the material about the point of dissection. Instead, any ultrasound horn allowing for the induction of vibrations within a confined region about the point of dissection may be utilized to practice the invention. For instance, an ultrasound horn having a consistent and narrow diameter may be used to induce vibrations within the wound confined to the region about the point of dissection. Consequently, exposing the material about the point of dissection to concentrated ultrasound vibrations may not be necessary.

As with dissection of the material to be debrided, the delivery of ultrasound inducing vibrations about the point of dissection does not have to occur simultaneously with the delivery of ultrasound energy to an area of the wound within the vicinity of the material to be debrided. Accordingly, one delivery may precede the other. For example, ultrasound energy may be first delivered to an area of the wound within the vicinity of the material to be debrided; then ultrasound vibrations may be delivered to induce vibrations within a confined region about the point of debridement.

Because the deliveries of ultrasound do not necessarily have to occur simultaneously to practice the invention, different horns may be utilized for each delivery. For instance, one horn held stationary above and/or swept over the wound may be used to deliver ultrasound energy to an area of the wound in the vicinity of the material to be debrided. A second horn could be placed in contact with the wound to deliver ultrasound vibrations inducing vibrations within a confined region about the point of debridement.

Accordingly, though specific embodiments of apparatuses and methods have been illustrated and described herein, it will be appreciated by those of ordinary skill in the art that any arrangement, combination, and/or sequence that is calculated to achieve the same purpose may be substituted for the specific embodiments shown. It is to be understood that the above description is intended to be illustrative and not restrictive. Combinations of the above embodiments and other embodiments as well as combinations and sequences of the above methods and other methods of use will be apparent to individuals possessing skill in the art upon review of the present disclosure.

It should be noted and appreciated that other benefits, mechanisms of action, and/or mechanisms of operation, in addition to those listed, may be elicited by methods in accordance with the present invention. The mechanisms of action and mechanisms of operation presented herein are strictly theoretical and are not meant in any way to limit the scope of this disclosure and/or the accompanying claims.

It should also be appreciated that elements described with singular articles such as "a", "an", and/or "the" and/or otherwise described singularly may be used in plurality. Likewise, it should be appreciated that elements described in plurality may be used singularly.

The scope of the claimed apparatus and methods should be determined with reference to the appended claims, along with the full scope of equivalents to which such claims are entitled.

I claim:

1. An apparatus comprising:
   a. a shaft comprising:
      i. a proximal end opposite a distal end,
      ii. at least one radial surface extending between the proximal end and the distal end, and
      iii. a longitudinal axis extending through the shaft from the proximal end to the distal end;
   b. a tip arranged at the distal end of the shaft and comprising:
      i. at least one radial surface;
      ii. a paraboloid cavity containing at least one wall and an opening within at least one of the radial surfaces of the tip, the opening having a peripheral edge lying in a plane, the plane of the opening being oriented generally parallel to the longitudinal axis of the shaft; and
      iii. a sharpened cutting member or plurality of sharpened cutting members at the opening of the cavity; and
   c. a channel or plurality of channels running through at least a portion of the shaft and comprising an opening within a wall of the cavity,
   wherein:
      the channel or plurality channels is adapted to receive a coupling medium for delivery to the cavity via the opening within the wall of the cavity; and
      the shaft and the tip are a single piece.

2. The apparatus of claim 1 further comprising at least one distal surface on the tip.

3. The apparatus of claim 2 further comprising a distal opening to the cavity of the tip within at least one of the distal surfaces on the tip.

4. The apparatus of claim 3 wherein the paraboloid cavity of the tip includes a focus and the focus lies outside the cavity.

5. The apparatus of claim 4 wherein the proximal end of the shaft is adapted for arrangement of a transducer, the apparatus further comprising a region of the tip wider than the shaft in at least one dimension oriented orthogonal to the longitudinal axis of the shaft.

6. The apparatus of claim 5 further comprising a parabola formed by the radial surfaces of the tip in at least two dimensions.

7. The apparatus according to claim 4 wherein said shaft and said tip are configured for vibrating in combination approximately in resonance at a frequency between approximately 15 kHz and approximately 3 MHz.

8. The apparatus of claim 7 wherein said shaft and said tip are configured for vibrating in combination approximately in resonance at a frequency of approximately 30 kHz.

9. The apparatus of claim 7 further comprising an ultrasound transducer arranged at the proximal end of the shaft.

10. The apparatus of claim 9 further comprising a generator configured for producing an electrical signal of a sufficient voltage to drive the transducer to induce the substructure formed by the shaft and tip to vibrate.

11. The apparatus according to claim 10 wherein the generator is configured for producing an electrical signal of a voltage sufficient to induce the substructure formed by the shaft and tip to vibrate approximately in resonance with the amplitude of the vibrations being between approximately 1 micron and approximately 100 microns.

12. The apparatus according to claim 11 wherein the generator is configured for producing an electrical signal of a voltage sufficient to induce the substructure formed by the shaft and tip to vibrate approximately in resonance with the amplitude of the vibrations being approximately 100 microns.

13. The apparatus according to claim 10 wherein the generator is configured for producing an electrical signal of a voltage sufficient to induce cavitations within the coupling medium.

14. The apparatus according to claim 13 wherein the generator is configured for producing an electrical signal of a voltage sufficient to atomize the coupling medium.

15. A method of wound debridement, comprising:
   a. selecting a surgical apparatus comprising:
      i. a shaft comprising:
         1. a proximal end opposite a distal end,
         2. at least one radial surface extending between the proximal end and the distal end, and
         3. a longitudinal axis extending through the shaft from the proximal end to the distal end; and
      ii. a tip arranged at the distal end of the shaft and comprising:
         1. at least one radial surface; and
         2. a paraboloid cavity containing at least one wall and an opening within at least one of the radial surfaces of the tip, the opening having a peripheral edge lying in a plane, the plane of the opening being oriented generally parallel to the longitudinal axis of the shaft; and
         3. a sharpened cutting member or plurality of sharpened cutting members at the opening of the cavity;
      iii. a channel or plurality of channels running through at least a portion of the shaft and comprising an opening within a wall of the cavity,
      wherein:
         the channel or plurality of channels is adapted to receive a coupling medium for delivery to the cavity via the opening within the wall of the cavity; and
         the shaft and the tip are a single piece; and
   b. debriding a wound with the selected surgical apparatus, the debriding comprising:
      i. vibrating the surgical apparatus approximately in resonance; and
      ii. scraping a portion of the tip across the wound,
   whereby ultrasonic energy emanates from the tip to the wound.

16. The method of claim 15 wherein the paraboloid cavity of the tip includes a focus and the focus lies outside the cavity.

17. The method of claim 16 further comprising vibrating the shaft and the tip in combination approximately in resonance at a frequency between approximately 15 kHz and approximately 3 MHz.

18. The method of claim 17, wherein the selected apparatus further comprises an ultrasound transducer arranged at the proximal end of the shaft and a generator and the method further comprises producing an electrical signal of a sufficient voltage to drive the transducer to induce the substructure formed by the shaft and tip to vibrate wherein the generator produces an electrical signal of a voltage sufficient to induce the substructure formed by the shaft and tip to vibrate approximately in resonance with the amplitude of the vibrations being between approximately 1 micron and approximately 100 microns.

19. The method of claim 18 further comprising producing an electric signal with the generator wherein electrical signal includes a voltage sufficient to induce cavitations within the coupling medium.

20. The method of claim 19 wherein the electrical signal includes a voltage sufficient to atomize the coupling medium.

* * * * *